US00PP15526P2

(12) United States Plant Patent
Oud

(10) Patent No.: US PP15,526 P2
(45) Date of Patent: Feb. 1, 2005

(54) *LOBELIA* PLANT NAMED 'LOBOUDTIS'

(50) Latin Name: *Lobelia erinus*
Varietal Denomination: Loboudtis

(75) Inventor: Johannes Simon Nicolaas Oud, Boyenkarspel (NL)

(73) Assignee: Syngenta Seeds B.V., Enkhuizen (NL)

( * ) Notice: Subject to any disclaimer, the term of this patent is extended or adjusted under 35 U.S.C. 154(b) by 17 days.

(21) Appl. No.: 10/706,714

(22) Filed: Nov. 12, 2003

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—Edouard G. Lebel

(57) ABSTRACT

A new *Lobelia* plant particularly distinguished by its spreading plant habit, strong branching, large flower size and light blue flower color.

1 Drawing Sheet

Latin name of the genus and species of the plant claimed: *Lobelia erinus.*
Varietal denomination: 'Loboudtis'.

BACKGROUND OF THE NEW PLANT

The present invention relates to a new and distinct cultivar of *Lobelia* plant.

The new cultivar is propagated by cuttings resulting from the cross between 'R616' and 'Z925'.

'R616' is a light blue flower color selection of own breeding, having a spreading plant habit, rather strong growth, good branching planthabit and being early flowering.

'Z925' is a blue flower color selection of own breeding, having a strong growth, trailing planthabit and being early flowering.

Neither 'R616' or 'Z925' has been patented.

As a result of this cross the present cultivar was created in 2000 in Enkhuizen, Netherlands and has been repeatedly asexually reproduced by cuttings in Enkhuizen over a 2 year period.

Is has been found to retain its distinctive characteristics through successive propagations and this novelty appears to be firmly fixed.

DESCRIPTION OF THE PHOTOGRAPH

This new *Lobelia* plant is illustrated by the accompanying photograph which shows blooms, buds and foliage of the plants in full color, the color shown being as true as can be reasonably obtained by conventional photographic procedures.

DESCRIPTION OF THE NEW CULTIVAR

The following detailed descriptions set forth the distinctive characteristics of this new *Lobelia.* The data, which defines these characteristics, were collected from asexual reproductions carried out in Enkhuizen, Netherlands. The plant history was taken on 12 weeks old plants.

Specification of differences with most resembling variety

| Characteristic | 'Loboudtis' | 'Blue Star' (Unpatented variety) | 'Ricardii' (Unpatented variety) |
|---|---|---|---|
| plant | | | |
| height | 10 cm | 10 cm | 10 cm |
| width | 30 cm | 35 cm | 35 cm |
| shape | spreading | spreading | spreading |
| flower color | | | |
| upper surface | 95C | 95B | 95B |
| lower surface | 95C | 100A | 95B |
| flower tube | 96D | 95C | 96D |

No descriptions of parentlines are available. The only info is mentioned as background of the new plant on page 1.

The plant:

*Classification — botanical.*—*Lobelia erinus.*

*Parentage.*—Female parent: A seedling named 'R616' is one of our seedlings from our R-generation of plants bred in 1991. Male parent: A seedling named 'Z925' is one of our seedlings from our Z-generation of plants bred in 1998.

*Growth habit.*—Spreading.

*Plant height.*—10 cm.

*Spreading area of plant.*—30 cm.

*Growth rate.*—Strong growth.

*Strength.*—Good, excellent.

*Branching character.*—Freely branching and lateral branching at ever node. Pinching will enhance branching. Branches strong and flexible.

*Blooming period.*—From May till October.

The stem:

*Diameter.*—2.0 mm.

*Texture.*—Smooth, slightly pubescent, glossy.

*Color RHS*—RHS 147A.

*Length of internode.*—15 mm, depending on the light conditions where the plant is propagated.

*Shape.*—(Tri)angular.

The foliage:

*Shape.*—Leaves simple, generally symmetrical and flat. Broadly ovate with rounded apex, obtuse to attenuate base and crenate margin.

*Texture.*—Slightly pubescent, glossy.

*Length.*—Young 40 mm, fully expanded 55 mm.

*Width.*—Young 10 mm, fully expanded 16 mm.

*Colour* (*both mature and juvenile phase of growth*).—Upper surface: RHS 147A. Lower surface: RHS 147A.

*Petiole.*—Length: 1.25 cm. Diameter: 2 mm. Color: RHS 147A.

*Veins.*—Color: RHS 147B.

The flower:

*Type and habit.*—Flower form at apical axils, usually one flower per axil. Flowers labiate, upper lip consisting of two small petals and lower lip consisting of three larger and broader petals. Petals are fused at base into a tube. Freely and continuously flowering. Flowers face outward. Flowers persistent. Texture, slightly pubescent. Oblong shape with acute apex and entire margin.

*Flower.*—Width: Upper petals 1 mm, lower petals 6 mm. Length: Upper petals 5 mm, lower petals 11 mm. Depth: 16 mm.

*Texture.*—Smooth, pubescent.

*Buds.*—Length: 7 mm. Diameter: 2 mm. Form: Tubular. Color: Light green.

*Flower color.*—Upper surface: RHS 95C. Lower surface: RHS 95C. Flower tube: RHS 96D.

*Sepals.*—No. of sepals: 5. Length: 6 mm. Width: 0.5 mm. Texture: Smooth, slightly pubescent. Color: RHS 146A.

*Flower stem.*—Length: 20 mm. Angle: Upright. Strength: Rigid, flexible. Color: RHS 147A. Diameter: 1 mm. Texture: Slightly pubescent, glossy. Shape: Round. Pubescence: Present.

*Flower throat.*—Color: Upper RHS 96D. Lower RHS 96D, spots R.H.S. 95B. Depth: 8 mm. Texture: Whiskered.

*Lastingness of blooms.*—Around 10–14 days, depending on temperature.

*Number of blooms.*—Approximately 150 during top of flowering, in 10 cm pot.

Between the 3 petals on the lower tip of the flower there are 2 small white spots, diameter 1 mm.

Reproductive organs:

*Androecium.*—Stamen number: 5. Anther shape: Oblong. Anther length: 1 mm. Pollen color: RHS 202B. Amount of pollen: Moderate.

*Gynoecium.*—Pistel length: 9 mm. Stigma shape: Bilobate. Stigma diameter: 1 mm. Stigma color: N87A. Style color: Light green. Ovary color: RHS 146A.

Seed development:

Some seed development has been observed on plants of the new *Lobelia*.

*Seed colour.*—Brown.

*Seed shape.*—Round.

*Seed size.*—Like dust.

*Seed amount.*—Around 1000–2000 seeds per fruit/pod.

Fruit:

*Fruitsize.*—Diameter: 2 mm. Length: 4 mm.

*Fruitcolor.*—RHS 147 A.

We claim:

1. A new and distinct variety of *Lobelia* plant, named 'Loboudtis', as illustrated and described.

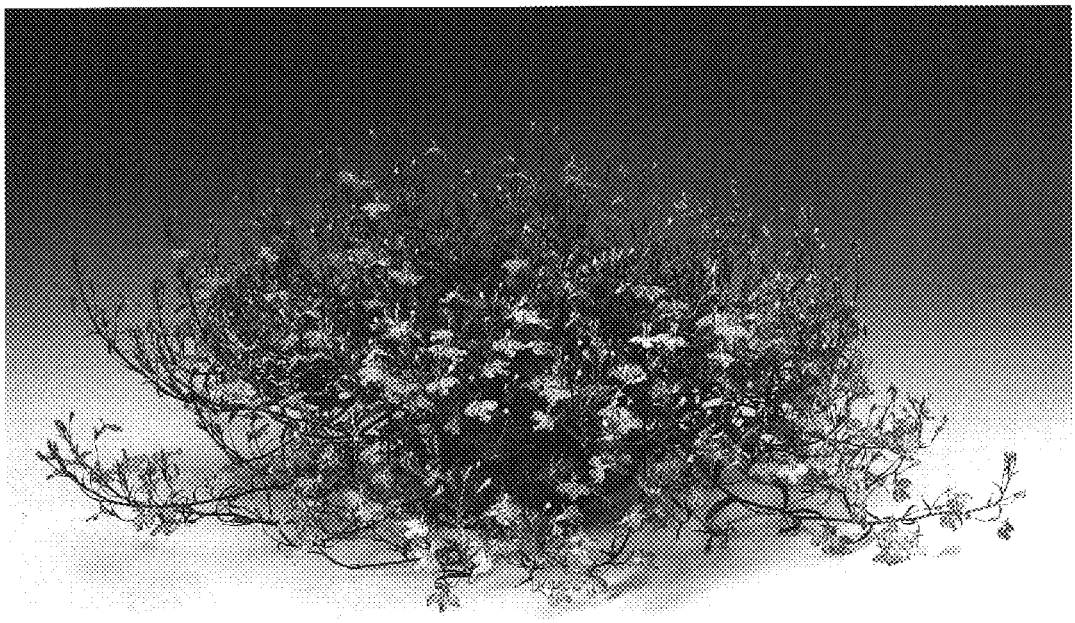

* * * * *